(12) United States Patent
Bourchteine et al.

(10) Patent No.: US 6,392,043 B1
(45) Date of Patent: May 21, 2002

(54) [INDOLE]NAPHTHOPYRANS, PREPARATION, COMPOSITIONS AND (CO) POLYMER MATRICES CONTAINING THEM, SYNTHESIS INTERMEDIATES

(75) Inventors: Konstantine Bourchteine, Jacques Durand; Olivier Breyne, Lyons, both of (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/530,554

(22) PCT Filed: Oct. 20, 1998

(86) PCT No.: PCT/US98/21930

§ 371 Date: Aug. 24, 2000

§ 102(e) Date: Aug. 24, 2000

(87) PCT Pub. No.: WO99/23071

PCT Pub. Date: May 14, 1999

Related U.S. Application Data

(60) Provisional application No. 60/070,381, filed on Jan. 5, 1998.

(30) Foreign Application Priority Data

Nov. 3, 1997 (FR) .............................................. 97 13769

(51) Int. Cl.$^7$ ...................... C07D 491/22; C07D 455/06
(52) U.S. Cl. ........................... 546/94; 359/244; 548/418
(58) Field of Search ........................... 548/418; 546/94; 359/244

(56) References Cited

U.S. PATENT DOCUMENTS

| 2,161,697 A | 6/1939 | Broeg et al. ................. 260/315 |
| 5,645,767 A | 7/1997 | Van Gemert ................. 252/586 |
| 5,651,923 A | * 7/1997 | Kumar et al. ............... 252/586 |

FOREIGN PATENT DOCUMENTS

| WO | 97/21698 | 6/1997 | ......... C07D/311/78 |

* cited by examiner

Primary Examiner—T. A. Solda
Assistant Examiner—Sonya Wright
(74) Attorney, Agent, or Firm—Angela N. Nwaneri; Peter Rogalskyj

(57) ABSTRACT

The object of the present invention is novel photochromic [indole]naphthopyran compounds and their methods of preparation.

11 Claims, No Drawings

[INDOLE]NAPHTHOPYRANS, PREPARATION, COMPOSITIONS AND (CO) POLYMER MATRICES CONTAINING THEM, SYNTHESIS INTERMEDIATES

This application is a 371 of PCT/US98/21930 filed Oct. 20, 1998 which claims benefit of provisional application No. 60/070,381 filed Jan. 5, 1998.

The present invention relates to novel [indole] naphthopyran compounds which have, in particular, photochromic properties. The invention also relates to:

compounds, synthesis intermediates, which are useful in the preparation of said [indole]naphthopyrans;

the preparation of said synthesis intermediates and said [indole]naphthopyrans;

photochromic compositions and photochromic ophthalmic articles (lenses for example) which contain said [indole]naphthopyrans.

The photochromic compounds are capable of changing color under the influence of a poly- or mono-chromatic light (UV for example) and of returning to their initial color when the luminous irradiation ceases, or under the influence of temperature and/or a poly- or mono-chromatic light different from the first.

The photochromic compounds find applications in various fields, e. g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

a high transmission in the absence of ultraviolets, a low transmission (high colorability) under solar irradiation, adapted coloration and discoloration kinetics, a tint acceptable to the consumer (gray or brown preferably) with preferably a maintenance of the chosen tint during the coloration and the discoloration of the lens, a maintenance of the performances, the properties, within a temperature range of 0–40° C., a significant durability, since these objectives sought after are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a gray or brown tint may necessitate the use of at least two photochromes of different colors, i. e. having distinct maximal absorption wavelengths in the visible. This association further imposes other requirements of the photochromic compounds. In particular, the coloration and discoloration kinetics of the (two or more) associated active photochromic compounds must be essentially identical. The same applies for their stability with time and also for their compatibility with a plastic or inorganic support.

Amongst the numerous photochromic compounds described in the prior art, benzopyrans and naphthopyrans may be cited which are described in patents or patent applications U.S. Pat. Nos. 3,567,605, 3,627,690, 4,826,977, 5,200,116, 5,238,981, 5,411,679, 5,429,744, 5,451,344, 5,458,814, WO-A-95 05382, FR-A- 2,718,447, WO-A-96 14596, WO-A-97 21698 and in the Research Disclosure No. 36144, which are of the formula below:

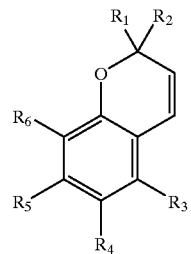

These compounds claim to satisfy the specifications defined above. In reality, if these compounds really do have one or more of the basic properties sought after, such as a high transmission in the absence of ultraviolets and a high colorability under solar irradiation, none of the compounds described hitherto have the complete combination of the properties sought after which are necessary for the production of satisfactory articles which may be manufactured industrially. In particular, none of these compounds is intrinsically gray or brown and the necessity of using an additional photochrome in order to obtain one of these two tints does subsist.

Several compounds having two intense and more or less complementary absorption bands in the visible have been described (WO-A-96 14596). These two bands are generally situated in the yellow/orange and in the violet/blue. However, the first band (yellow) is far less intense and the stability of these compounds vis-a-vis the photochromic ageing is far from being satisfactory.

Although the general formula IA of the patent application WO-A-97 21698 includes [indole]naphthopyrans, such [indole]naphthopyrans are not described in this prior art document insofar as said document does not indicate any method of synthesizing said [indole]napthopyrans. [Indeno] naphthopyrans are effectively described in said document but no means of access to the [indole]naphthopyrans is suggested. It is to the credit of the Applicant to have proposed such a means of access (an efficient synthesis method) and to have discovered that this type of compound possesses particularly advantageous photochromic properties. More specifically, they possess a particularly intense first band in the yellow/orange, a second band of high $\lambda_{max}$ and a high colorability, even at 40° C., associated with rapid discoloration kinetics.

Thus, the object of the present invention is [indole] naphthopyran compounds of formula (I):

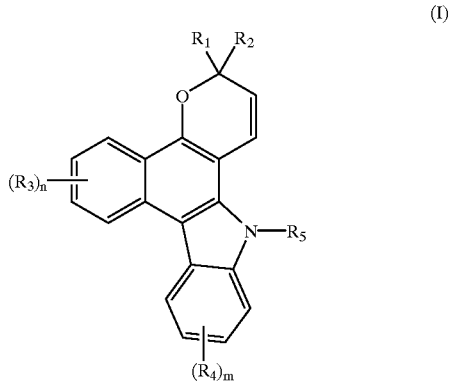

in which:
  $R_1$ and $R_2$, identical or different, independently represent:
    hydrogen,
    a linear or branched alkyl group having 1 to 12 carbon atoms,
    a cycloalkyl group having 3 to 12 carbon atoms,
    an aryl or heteroaryl group having 6 to 24 carbon atoms or 4 to 24 carbon atoms respectively in its basic structure and at least one heteroatom selected from sulfur, oxygen and nitrogen; said basic structure optionally being substituted with at least one substituent selected from:
      a halogen and notably fluorine, chlorine and bromine,
      a linear or branched alkyl group having 1 to 12 carbon atoms,
      a linear or branched alkoxy group having 1 to 12 carbon atoms,
      a linear or branched haloalkyl or haloalkoxy group corresponding respectively to the ($C_1$–$C_{12}$) alkyl and ($C_1$–$C_{12}$) alkoxy groups above substituted with at least one halogen atom and notably a fluoroalkyl group of this type,
      a linear or branched alkenyl group having 2 to 12 carbon atoms and notably a vinyl group or an allyl group,
      an —$NH_2$ group,
      an —NHR group, R representing a linear or branched alkyl group having 1 to 6 carbon atoms,

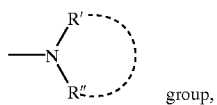 group,

R' and R", identical or different, representing independently a linear or branched alkyl group having 1 to 6 carbon atoms or representing, together with the nitrogen atom to which they are bound, a 5- to 7-membered ring which can comprise at least one other heteroatom selected from oxygen, sulfur and nitrogen, said nitrogen optionally being substituted with an R''' group, a linear or branched alkyl group, having 1 to 6 carbon atoms,
    a methacryloyl group or an acryloyl group,
    an epoxy group of formula:

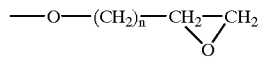

in which n=1, 2 or 3,
    an aralkyl or heteroaralkyl group, the linear or branched alkyl group having 1 to 4 carbon atoms and the aryl and heteroaryl groups having the definitions given above, or
    said two substituents $R_1$ and $R_2$ together form an adamantyl, a norbornyl, a fluorenylidene, a di($C_1$–$C_6$) alkylanthracenylidene or a spiro($C_5$–$C_6$)cycloalkylanthracenylidene group; said group optionally being substituted with at least one of the substituents listed above for $R_1$, $R_2$: aryl or heteroaryl group;
  $R_3$ and $R_4$, identical or different, independently represent:
    hydrogen,
    a halogen, and notably fluorine, chlorine or bromine,
    a linear or branched alkyl group having 1 to 12 carbon atoms (advantageously 1 to 6 carbon atoms),
    a cycloalkyl group having 3 to 12 carbon atoms,
    a linear or branched alkoxy group, having 1 to 12 carbon atoms (advantageously 1 to 6 carbon atoms)
    a haloalkyl, a halocycloalkyl or haloalkoxy group corresponding respectively to the alkyl, cycloalkyl, alkoxy groups above, substituted with at least one halogen atom, notably selected from fluorine, chlorine and bromine,
    an aryl or heteroaryl group having the same definition as that given above for $R_1$, $R_2$,
    an aralkyl or heteroaralkyl group, the linear or branched alkyl group having 1 to 4 carbon atoms and the aryl and heteroaryl groups having the same definitions as those given above for $R_1$, $R_2$,
    an amine or amide group: —$NH_2$, —NHR, —$CONH_2$, —CONHR,

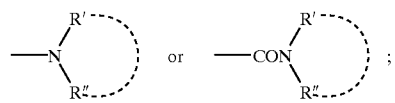

R, R', R" having their respective definitions given above for the amine substituents of the $R_1$, $R_2$ values: aryl or heteroaryl,
    an —$OCOR_6$ or —$COOR_6$ group, $R_6$ representing a straight or branched alkyl group having 1 to 6 carbon atoms or a cycloalkyl group having 3 to 6 carbon atoms or a phenyl group optionally substituted with at least one of the substituents listed above for the $R_1$, $R_2$ values: aryl or heteroaryl;
  m and n are, independently, integers of 0 to 4;
  $R_5$ represents:
    hydrogen,
    a linear or branched alkyl group having 1 to 12 carbon atoms (advantageously 1 to 6 carbon atoms),
    a cycloalkyl group having 3 to 12 carbon atoms,
    a linear or branched alkenyl group having 2 to 12 carbon atoms and notably a vinyl group or an allyl group,
    a phenyl or benzyl group, optionally substituted with at least one of the substituents listed above for the $R_1$, $R_2$ values: aryl or heteroaryl,
    a —$COR_7$, —$COOR_7$ or $CONHR_7$ group, $R_7$ representing a straight or branched alkyl group having 1 to 6 carbon atoms or a cycloalkyl group having 3 to 6 carbon atoms or a linear or branched alkenyl group having 2 to 12 carbon atoms and notably an allyl group or a phenyl or benzyl group optionally substituted with at least one of the substituents listed above for the $R_1$, $R_2$ values: aryl or heteroaryl,
    a methacryloyl group or an acryloyl group,
    an epoxy group of formula:

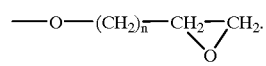

in which n=1, 2 or 3.
  Amongst said compounds of formula (I) above, those which are of formula (I1) below are preferred:

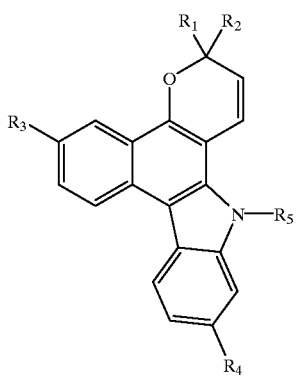

(II)

in which:
- $R_1$ and/or $R_2$, identical or different, independently represent optionally substituted aryl or heteroaryl groups whose basic structure is selected from those of the phenyl, naphthyl, biphenyl, pyridyl, furyl, benzofuryl, dibenzofuryl, N—($C_1$–$C_6$)alkylcarbazole, thienyl, benzothienyl, dibenzothienyl and julolidinyl groups; $R_1$ and/or $R_2$ advantageously representing a phenyl group substituted in the para position;
- $R_3$ and $R_4$, identical or different, independently represent hydrogen, a linear or branched alkoxy group having 1 to 6 carbon atoms, a halogen, a linear or branched alkyl group having 1 to 6 carbon atoms, a morpholino group or a dialkylamino group—NR'R" in which R' and R" independently represent a linear or branched alkyl group having 1 to 6 carbon atoms;
- $R_5$ represents hydrogen, a linear or branched alkyl group having 1 to 6 carbon atoms, an optionally substituted phenyl or benzyl group, a —$COR_7$, —$COOR_7$, or $CONHR_7$ group, $R_7$ representing a straight or branched alkyl group having 1 to 6 carbon atoms or an optionally substituted phenyl or benzyl group.

Amongst the substituents ($R_1$, $R_2$, $R_5$) of the compounds of the invention, they are some which comprise and/or form at least one polymerizable and/or cross-linkable reactive group. The presence of such reactive groups can prove to be advantageous. Thus, the present invention includes, in its first object, [indole]naphthopyran compounds, such as defined above, whose structure includes at least one polymerization and/or cross-linking reactive group; said group consisting of an alkenyl group, advantageously vinyl or allyl, or of a methacryloyl, acryloyl or epoxy group.

Thus, the compounds of the invention which belong to this class can be grasped as monomers, of different nature or not, which can react with themselves and/or with other co-monomers in order to form homopolymers and/or copolymers which are carriers of a photochromic functionality (insofar as said monomers of the invention bear said photochromic functionality) and possess the mechanical properties of macromolecules.

It follows that another object of the present invention is formed by these linear or branched homopolymers or copolymers, at least in part constituted by the compounds of the invention.

Similarly, the above-mentioned compounds of the invention can be envisaged as cross-linking agents having reactive functions which can allow bridges between chains of photochromic or non-photochromic polymers. The reticulates (products of cross-linking) which can be obtained also constitute another object of the present invention.

The compounds of the invention—[indole]naphthopyrans of formula (I)—can be obtained in a general manner by the condensation of a compound of formula (II) below:

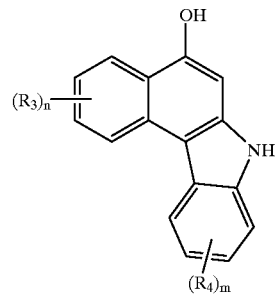

(II)

in which $R_3$, $R_4$, m and n are as defined with reference to formula (I) above;

with a propargylic alcohol derivative of formula (III) below:

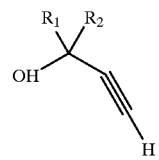

(III)

in which $R_1$ and $R_2$ are as defined with reference to formula (I) above (the condensation reaction can be carried out in solvents such as toluene or tetrahydrofuran in the presence of a catalyst such as para-toluenesulfonic acid or bromoacetic acid)

or with, in the presence of titanium tetralkoxide (especially titanium tetraethoxide), an aldehyde of formula (III') below

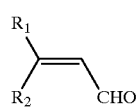

(III')

in which $R_1$ and $R_2$ are as defined with reference to formula (I) above (see EP-A-0 562 915 for example).

The compounds of the invention obtained by this condensation and which are of formula ($I_a$) below (formula (I) in which $R_5$=H) are then optionally, for the preparation of the compounds of formula (I) in which $R_5 \neq H$ (formula ($I_b$) below), after deprotonation in the presence of sodium hydride, reacted with a suitable electrophilic compound of formula $R_5X$, in which X is a leaving group: which can be schematized by the reaction below:

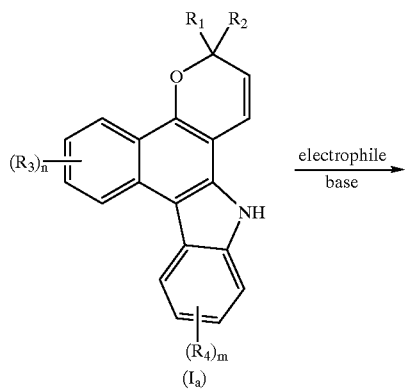

(Iₐ)

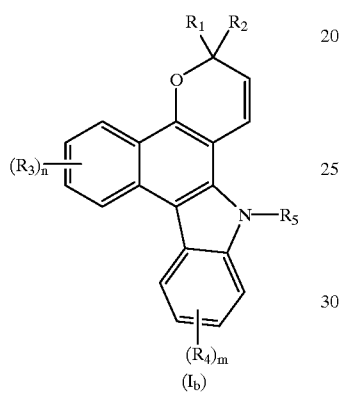

(Iᵦ)

Thus, for this synthesis of the [indole]naphthopyrans of the invention, novel compounds of formula (II) are used on the one hand, and compounds of formula (III) or the corresponding aldehyde derivatives on the other.

Said compounds of formula (III) are known to the person skilled in that art and are obtained from the corresponding ketone according to a method described notably in the patent application WO-A-96 14596. The ketone is itself commercial or is prepared according to known methods such as the Friedel Crafts reaction (cf. WO-A-96 14596 and cited references). The aldehyde derivatives of (III) are obtained by a rearrangement in acid medium (cf. *J. Org. Chem.* 1977, 42, 3403).

Said original compounds of formula (II) above open up an original and magnificent route to the preparation of [indole]naphthopyrans of formula (I) of the invention.

Thus, the other objects of the present invention consist of:

the method of preparing said [indole]naphthopyrans from said compounds of formula (II) (method specified above);

said compounds of formula (II) themselves; and the method of preparing said compounds of formula (II); a method described below.

Said compounds of formula (II) are obtained according to an original synthesis scheme whose various steps are known to the person skilled in the art, or are adapted from the literature. Said synthesis scheme comprises:

submitting the compound of formula (V)

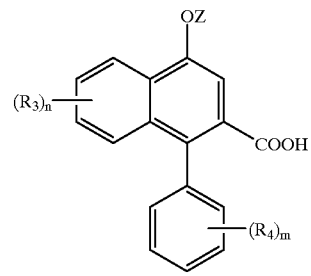

in which $R_3$, $R_4$, m and n are as defined with reference to formula (I)

and Z represents hydrogen or a labile protecting group such as an acetyl group;

to a Curtius rearrangement, in order to obtain the compound of formula (VII):

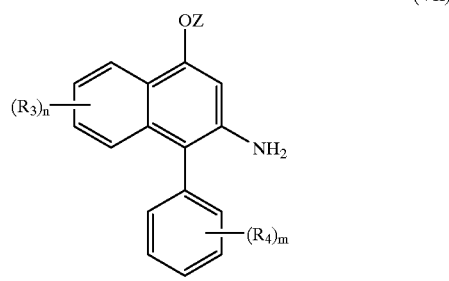

activating said compound of formula (VII) by diazotation in the presence of $HNO_2$, and reacting said activated compound with sodium azide in order to obtain the corresponding azide of formula (VIII):

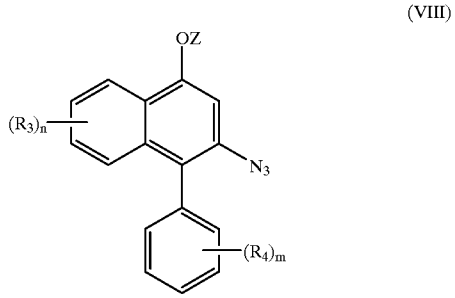

photochemically decomposing said azide in order to obtain the corresponding carbazole, followed if necessary (in the hypothesis when Z≠H), by the deprotection of the hydroxyl group.

The acids of formula (V) (formula ($V_a$) when Z=H; formula ($V_b$) when Z≠H), whose hydroxyl function is protected or not by a labile Z group, are easily accessible from the corresponding benzophenones according to a synthesis route described in the application WO-A-96 14596.

Said acids undergo, in a way known per se, a Curtius rearrangement in order to generate the amines of formula (VII). It is highly recommended to carry out said Curtius rearrangement under mild conditions according to the reaction scheme below:

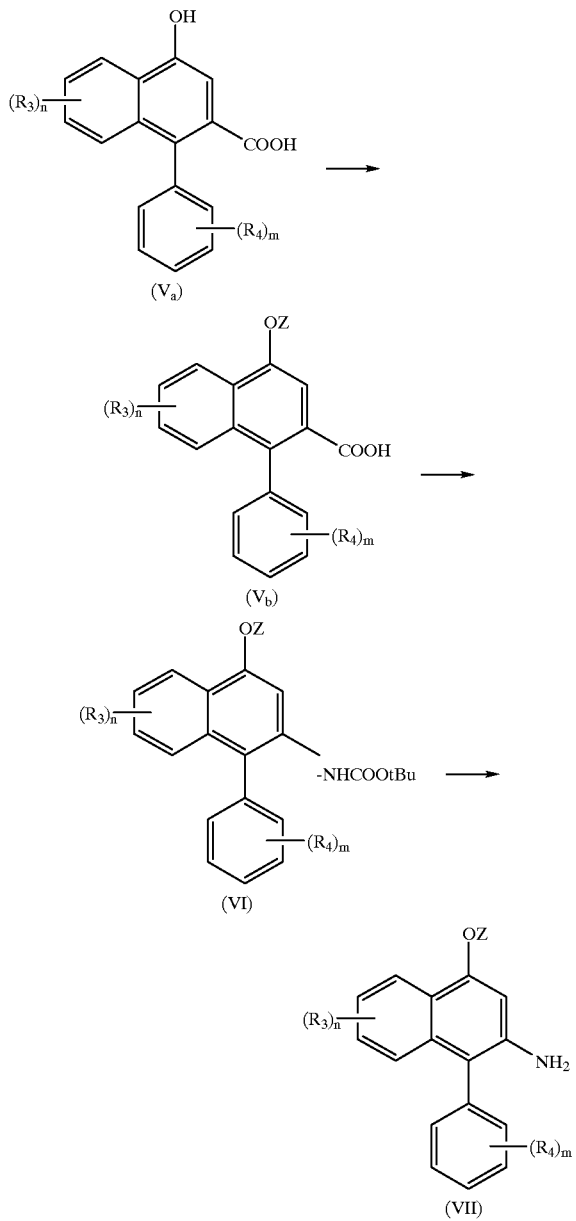

(with Z≠H; notably Z=acetyl group).

The $(V_a) \rightarrow (V_f)$ transformation can be deduced from the method described in J.Am.Chem.Soc.,1972, 94, 6203–6205. The Curtius rearrangement $(V_b) \rightarrow (VI)$ is in general carried out in refluxing toluene in the presence of diphenylphosphorazide (DPPA), triethylamine ($NEt_3$) and tert-butanol (tBuOH).

The protected amine function of the compound (VI) is deprotected in order to lead to the compound (VII), generally with trifluoroacetic acid in dichloromethane.

The aromatic nucleophilic substitution via the diazotation of an arylamine (transformation (VII)→(VIII)) is well known to the person skilled in the art and is described notably in Vogel's Textbook of Practical Organic Chemistry (fifth edition, p. 922 and seq.).

Finally, the azide (VIII), by photochromic rearrangement, leads to the carbazole of formula (II). This type of rearrangement of an ortho-azidobiphenyl is notably described in *The Chemistry of Heterocycles* (Georg Thieme Verlag Stuttgart, New York, 1995), as means of access to carbazoles.

In the hypothesis wherein Z≠H, the hydroxyl function of the carbazole obtained must still be deprotected. This deprotection step is carried out in a manner known per se. Thus, in order to deacylate such a function, the mild conditions below are advantageously operated under: in tetrahydrofuran with 0.5 N sodium hydroxide at 0° C.

It is to the credit of the Applicant to have prepared and tested the original compounds of formula (I) described above; said compounds possess particularly advantageous photochromic properties. More specifically, these novel compounds possess a high colorability, with higher λ.max values that the known naphthopyrans of analogous structure.

Furthermore, these compounds are compatible with the organic polymer or inorganic material support matrices both in the form included in said matrices and in the form of a coating of said matrices.

In solution or in a polymer matrix, the compounds according to the invention are colorless or faintly colored in the initial sate and rapidly develop an intense coloration under UV light (365 nm) or a light source of the solar type. Finally, they regain their initial coloration when the irradiation ceases.

According to another of its objects, the present invention relates to the use of said compounds of formula (I) of the invention as photochromic agents. In other words, the Applicant presently proposes:

novel photochromic compounds which consist of the naphthopyran derivatives such as defined above ([indole]naphthopyrans), taken alone or in a mixture of themselves and/or with at least one other photochromic compound of another type and/or with at least one non-photochromic coloring agent;

novel photochromic compositions which comprise at least one naphthopyran derivative ([indole]naphthopyrans) such as defined above and/or at least one (co)polymer and/or reticulate having at least one of said naphthopyran derivatives of the invention in its structure. Such photochromic compositions can contain at least one other photochromic compound, of another type and/or at least one non-photochromic coloring agent and/or at least one stabilizing agent.

Said photochromic compounds of another type, non-photochromic coloring agents, and stabilizing agents are prior art products known to the person skilled in the art.

Combinations of photochromic compounds of the invention and/or photochromic compounds of the invention and photochromic compounds of another type according to the prior art are particularly recommended which are suitable for generating gray or brown tints.

The compounds of the invention, notably as photochromic compounds, can be used in solution. Thus, a photochromic solution can be obtained by dissolving at least one of said compounds in an organic solvent such as toluene, dichloromethane, tetrahydrofuran or ethanol. The solutions obtained are in general colorless and transparent. When exposed to sunlight, they develop a high coloration and regain the colorless state when they are placed in an area of less exposure to the sun's rays or, in other words, when they are no longer submitted to UV. In general, a very low concentration of product (of the order of 0.01 to 5% by weight) is sufficient to obtain an intense coloration.

The compounds of the invention ([indole]naphthopyrans of formula (I)) can also be used as a photochromic material dispersed uniformly in the mass or on the surface of a polymer matrix. In fact, the most interesting applications of the compounds of the invention are those in which the photochrome is dispersed uniformly within or on the surface of a polymer, copolymer or mixture of polymers. The (co)polymer matrix which comprises said photochrome of the invention (at least one, in a free form, and/or in the form of a (co)polymer and/or reticulate, and/or in the form of a photochromic composition, such as defined above) constitutes another object of the present invention.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerizable matrices, depositing this mixture on a surface or in a mold, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

In accordance with a variant of this object of the invention, it is also envisagable to graft the photochromes onto the (co)polymers. Thus, the invention also relates to the (co)polymers grafted by at least one of the photochromes described above. Thus, the expression "(co)polymer matrix comprising at least one photochrome of the invention" means both matrices which comprise said photochrome in their mass and on their surface, and matrices grafted by said photochrome.

The following products can be mentioned as examples of polymeric materials preferred for optical applications of the photochromic compounds according to the invention:
- optionally halogenated alkyl, cycloalkyl, aryl or aralkyl poly (mono-, di-, tri- or tetra-) acrylate or poly (mono-, di-, tri- or tetra-) methacrylate or having at least one ether and/or ester and/or carbonate and/or carbamate and/or thiocarbamate and/or urea and/or amide group,
- polystyrene, polyether, polyester, polycarbonate (e. g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral,
- copolymers of at least two types of co-polymerizable monomers selected from precursor monomers of the polymers listed above (notably selected from (meth) acrylics. vinyls, allyls, and mixtures thereof), and resins, having a nanobiphasic structure, obtained by copolymerisation of a mixture of at least one or more difunctional monomers of type (a) and one or more difunctional monomers of type (b):
the difunctional monomer(s) of type (a) being of one or the other of formulae (A) and (A') hereinafter:

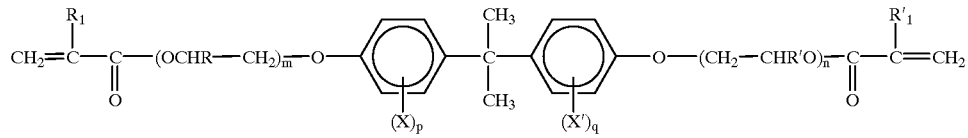

in which:
$R_1$, $R'_1$, R and R', identical or different, independently are a hydrogen or a methyl group;
m and n are, independently, integers between 0 and 4 inclusive; and are advantageously independently equal to 1 or 2;
X and X', identical or different, are a halogen and preferably represent chlorine and/or bromine;
p and q are, independently, integers between 0 and 4 inclusive;

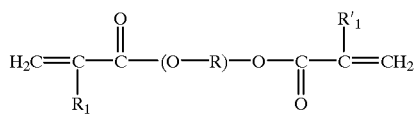

in which:
$R_1$ and $R'_1$, identical or different, independently are a hydrogen or a methyl group;
R is a linear or branched alkyl radical having from 2 to 8 carbon atoms, a cycloalkyl radical having from 3 to 6 carbon atoms, an ether radical of formula (R'—O—R") in which R' and R", identical or different, independently are a linear or branched alkyl radical having from 2 to 4 carbon atoms;
the difunctional monomer(s) of type (b)—long chain alkenic difunctional oligomer—being of one or the other of formulae (B), (B') and (B") hereinafter:

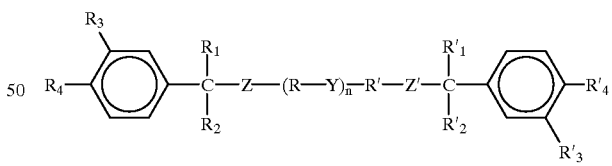

in which:
$R_1$, $R'_1$, $R_2$ and $R'_2$, identical or different, independently are hydrogen or a linear or branched alkyl radical, advantageously linear, having from 1 to 4 carbon atoms; and correspond particularly advantageously to a methyl group;
$R_3$ and $R_4$, different, are independently one hydrogen and the other an alkenyl radical having from 2 to 6 carbon atoms, advantageously from 2 to 4 carbon atoms and particularly advantageously an isopropenyl radical;
$R'_3$ and $R'_4$, different, are independently one hydrogen and the other an alkenyl radical having from 2 to 6 carbon atoms, advantageously from 2 to 4 carbon atoms and particularly advantageously an isopropenyl radical;

Z represents a carbamate function (—NH—CO—O—), a thiocarbamate function (—NH—CO—S—) or a urea function (—NH—CO—NH—);

Z', independent from Z and advantageously respectively with respect to Z, represents a carbamate function (—O—CO—NH—), a thiocarbamate function (—S—CO—NH—) or a urea function (—NH—CO—NH—);

R' represents a linear or branched alkyl radical having from 2 to 4 carbon atoms;

R, identical or different when $n \geq 2$, is a linear or branched alkyl radical having from 2 to 4 carbon atoms;

Y, identical or different when $n \geq 2$, is oxygen or sulfur;

n is an integer defined in such a way that the total number of carbon atoms contained in the long chain situated between the two motifs Z and Z' be at least equal to 18 and is advantageously between 18 and 112 inclusive;

above) and at least one long-chain difunctional alkenic monomer (of type (b) above). Such a combination enables obtaining a very satisfactory compromise of the photochromic properties/mechanical properties.

The [indole]naphthopyrans of formula (I) according to the invention have very interesting photochromic properties within such resins.

With reference to said resins, it is specified that the intervention:

of tetraethoxylated Bisphenol A dimethacrylate (compound of formula (A) in which R=R'=H, $R_1=R'_1=CH_3$, m=n=2 and p=q=0) as difunctional monomers of type (a) is most particularly recommended; and the intervention of long-chain polyoxyalkylene difunctional alkenic oligomers resulting from the reaction of at least one alkenylisocyanate (especially 3-isopropenyl-α,α-dimethylbenzylisocyanate or m-TMI®) and at least one diamine of formula $H_2N—(R—O)_n—R'—NH_2$, in which R and R' are as defined above in reference to the formula (B) (a $C_2$–$C_4$ alkyl radical) as difunctional "monomers" of type (b) is most particularly recommended.

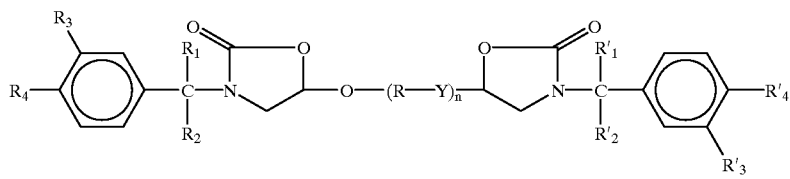

in which:

$R_1, R_2, R_3, R_4, R'_1, R'_2, R'_3, R'_4$, R and Y are such as defined hereinabove with reference to formula (B);

n is an integer defined in such a way that the total number of carbon atoms contained in the long chain of the motif $(R—Y)_n$ be at least equal to 22 and is advantageously between 22 and 104 inclusive;

Finally, it is specified in general terms that within said resins, the amount of monomer(s) of type (a) is between 40 and 99 parts by weight for 100 parts by weight of the mixture of monomers of type (a) and (b).

The amount of photochrome used in the (co)polymer matrix depends upon the degree of darkening desired. Usually, between 0.001 and 20% by weight of it is used.

The photochromic compounds according to the invention can be used alone or in a mixture with other products in

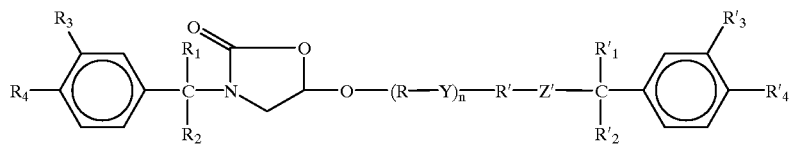

in which:

$R_1, R_2, R_3, R_4, R'_1, R'_2, R'_3, R'_4$, R, R' and Y are such as defined hereinabove with reference to formula (B);

Z' is a carbamate function (—O—CO—NH—) or Z' is a thiocarbamate function (—S—CO—NH—);

n is an integer defined in such a way that the total number of carbon atoms contained in the long chain of the motif $(R—Y)_n$ be at least equal to 22 and is advantageously between 22 and 104 inclusive.

Such resins have been described by the Applicant in the French patent Application FR 97 05458 filed on the May 2, 1997. These resins combine within them at least one short-chain difunctional (meth)acrylic monomer (of type (a)

order to form a composition which can be a solid or a liquid, in solution or in suspension for example, as has already been indicated above. These compositions, which constitute an object of the invention as already indicated above, can therefore comprise the compounds of the invention and other additional photochromic compounds enabling obtaining dark colorations, gray or brown for example, desired by the public in applications such as ophthalmic or solar spectacles trade. These additional photochromic compounds can be those known to the person skilled in the art and described in the literature, e. g. chromenes (U.S. Pat. Nos. 3,567,605, 5,238,981, WO-A-94 22850, EP-A 562 915), spiropyrans or naphthospiropyrans (U.S. Pat. No. 5,238, 981) and spiroxazines (Crano et al., "Applied Photochromic Polymer Systems", Ed. Blackie & Son Ltd, 1992, chapter 2).

Said compositions according to the invention can also comprise:
- non-photochromic coloring agents which enable adjusting the tint,
- and/or one or more stabilizing agents. such as an anti-oxidizing agent for example,
- and/or one or more anti-UV,
- and/or one or more anti-radicals,
- and/or one or more photochimic excited state deactivators.

These additives can notably enable improving the durability of said compositions.

According to another of its aspects relative to the application of the compounds of the invention, another object of the present invention is ophthalmic articles, such as articles for the ophthalmic and solar spectacles trade, which comprise at least one compound according to the invention and/or at least one (co)polymer and/or reticulate formed, at least in part, from compound(s) of the invention and/or at least one composition containing at least one compound of the invention and/or at least one matrix, such as defined above, of an organic polymer material or an inorganic material or even of an inorganic-organic hybrid material incorporating therein at least one compound of the invention.

In practice, the articles most particularly covered by the present invention are photochromic ophthalmic or solar lenses, glazing (window panes for buildings, locomotion engines, automobiles), optical devices, decorative devices, solar protection devices, information storage, . . . .

The present invention is illustrated by the example that follows of synthesis and photochromic validation, of a compound of the invention ([indole]naphthopyran). Said compound of the invention is compared to a prior art compound C1.

EXAMPLE 1

Synthesis of Compound (1) ($R_1=R_2=$p-$C_6H_4OCH_3$, $R_3=R_4=$H, $R_5=CH_3$)

Step 1: 10.58 g of acid (of formula $V_a$) ($R_3=R_4=$H) obtained from the corresponding benzophenone according to WO-A-96 14596 are added at ambient temperature to a suspension of 4 g of NaH (60% in a mineral oil) in 200 ml of THF. After stirring under reflux for 30 min, the mixture is cooled to 0° C. and 3.12 ml of acetyl chloride are added. After stirring for 1 h 30 at ambient temperature and then under reflux for 30 min, the reaction mixture is hydrolyzed with 100 ml of water, then extracted with 200 ml of ethyl acetate. The organic phase is extracted with 2×100 ml of 1N sodium hydroxide solution, and the combined aqueous phases are acidified and then extracted with 2×100 ml of ethyl acetate. After drying over magnesium sulfate and evaporation of the solvents, a recrystallization in a mixture of diisopropyl ether/heptane enables isolating 6.36 g of beige crystals (compound of formula $V_b$).

Step 2: The product obtained from step 1 is placed in suspension in 100 ml of toluene, 3.1 ml of triethylamine are then added. Stirring is carried out for 10 min at ambient temperature, 5.39 ml of diphenylphosphorazide are added and stirring is continued for 30 min at ambient temperature. 2.36 ml of tert-butanol are added and stirring is continued overnight under reflux. After evaporation of the solvent, the mixture is taken up into ethyl acetate and is washed with a solution of sodium bicarbonate. After drying over magnesium sulfate and evaporation of the solvents, the brown oil obtained is crystallized from methanol giving 5.28 g of a white solid (compound of formula VII protected).

Step 3: The product of step 2 is placed in solution at 0° C. in 90 ml of a 1/1 mixture of trifluoroacetic acid in dichloromethane. After stirring at 0° C. for 30 min, the reaction mixture is diluted in 150 ml of toluene and the solvents are evaporated under vacuum. The oil obtained is taken up into 100 ml of ethyl acetate and then washed with a solution of sodium bicarbonate. After drying over magnesium sulfate, the evaporation of the solvents allows isolating 4.03 g of a just yellow oil (compound of formula VII deprotected).

Step 4: The product of step 3 is dissolved in 60 ml of acetone and is stirred at 0° C. 10 ml of 12N HCl are added, then 1.105 g of sodium nitrite (in solution in the minimum of water). Stirring is continued for 10 min at 0° C., 1.3 g of solid sodium azide are then cautiously added (Beware of the potential release of hydrazoic acid!). This is stirred for 15 min at 0° C., diluted in 200 ml of ethyl acetate and is poured carefully into a solution of potassium carbonate. The aqueous phase extracted with 2×50 ml of ethyl acetate and the combined organic phases are dried over magnesium sulfate and evaporated to dryness. After recrystallization from methanol, 3.74 g of a gray powder are isolated (compound of formula VIII).

Step 5: 1.35 g of the product of step 4 are dissolved in 30 ml of THF and the solution obtained is placed in a quartz recipient. The reaction mixture is irradiated with 2 UV lamps (15 W, 254 and 365 nm, Prolabo, tubes for darkroom CN 15) for 4 days. The solvent is then evaporated. After recrystallization from methanol, 770 mg of a yellow powder are isolated (compound of formula II protected).

Step 6: A solution of 275 mg of product of step 5 in 20 ml of THF is cooled to 0° C. and 10 ml of a cooled 0.5 N NaOH solution are added. The reaction mixture is stirred for 20 min at 0° C., the reaction is then quenched with 10 ml of a 1N solution of HCl. This is extracted with 100 ml of ethyl acetate, the organic phase is dried over magnesium sulfate and the solvents are evaporated. 225 mg of a just yellow solid are thus obtained (compound of formula II).

Step 7: A catalytic amount (spatula tip) of bromoacetic acid is added to a solution of 150 mg of the product of step 6 and 174 mg of bis(para-methoxyphenyl)propargylic alcohol in 20 ml of toluene. After stirring overnight under reflux, the reaction mixture is purified over neutral alumina (eluent: diisopropyl ether/EtOAc) and the photochrome is recrystallised from a mixture of diisopropyl ether/heptane giving 130 mg of a green solid (compound of formula I in which $R_5=$H).

Step 8: A solution of 120 mg of the product of step 7 in 5 ml of anhydrous THF is cooled to 0° C. 50 mg of NaH (60% in a mineral oil) and 0.2 ml of methyl iodide are then added successively. The reaction mixture is stirred for 15 minutes at 0° C. and the reaction is then quenched with 10 ml of a saturated ammonium chloride solution. This is extracted with 100 ml of EtOAc, dried over $MgSO_4$ and the solvent is evaporated. After recrystallization from a mixture of diisopropyl ether/heptane, 65 mg of product (1) are isolated as a green solid (compound of formula I in which $R_5=CH_3$).

EXAMPLE 2

Compound C1

The prior art compound C1, described in RD 31 144, of formula:

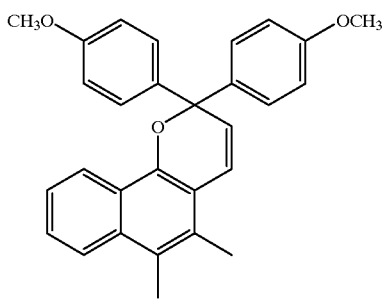

has been considered. This compound is commercially available.

EXAMPLE 3

The photochromic properties of said compounds (1) and C1 were evaluated.

To this end, said compounds are incorporated in a matrix at the rate of about 0.05% by weight.

A mixture of the starting materials is in fact carried out, whose nature and intervening amounts are specified below; the mixture is poured into a lens mold of 2 mm thickness which is then submitted to a hardening cycle of 2 hours at 75° C. and then 1 hour at 120° C.

The precursor starting materials of the matrix are:

0.05 parts by weight of the photochromic coloring agent: compound (1) or C1; for 11.5 parts by weight of divinylbenzene;

2.9 parts by weight of 2-ethylhexylmethacrylate;

14.4 parts by weight of benzylmethacrylate;

0.5 parts by weight of n-dodecanethiol;

0.2 parts by weight of AMBN (2,2'-azobis(2-methylbutyronitrile) provided by AKZO (Perkadox®));

42.3 parts by weight of DIACRYL 121 from AKZO Chimie (tetraethoxylated Bisphenol A dimethacrylate);

28.8 parts by weight of an isopropenyl oligomer of the type [m-TMI®+poly(oxyethylene)diamine (M=600)+ poly(oxyethylene)diamine (M=2000)].

Said isopropenyl oligomer was obtained by reaction of 36.13% by weight of 3-isopropenyl-α,α-dimethylbenzylisocyanate (CYTEC);

44.71% by weight of JEFFAMINE® ED 600 (polyoxypropylene diamines marketed by TEXACO);

19.16% by weight of JEFFAMINE® ED 2 000 (polyoxypropylene diamines marketed by TEXACO).

Said matrix, containing said photochromic compounds in its mass is exposed to a UV radiation (source: xenon lamp). The $\lambda_{max}$ values in the visible and the discoloration kinetics are given in the Table below.

| Compound | Structure | λ uv nm | $\lambda_1$ visible nm | $\lambda_2$ visible nm | discoloration kinetics ($T_{1/2}$) | $DO_1/DO_2$ 25° C. | $DO_1/DO_2$ 40° C. |
|---|---|---|---|---|---|---|---|
| (1) | 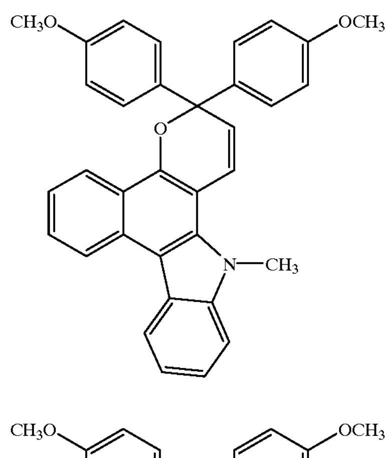 | 402 | 452 | 564 | 36 s | 0.84/0.45 | 0.37/0.20 |
| C1 | | 365 | 424 | 503 | 92 s | 0.59/0.99 | 0.27/0.46 |

It is shown by these measurements that the compound of the invention has higher $\lambda_{max}$ values than the analogous compound without the indole ring ringed in position 5,6 of the naphthopyran. Furthermore, the presence of the two absorption bands of the compounds of the invention allow covering a greater range of the visible spectrum. Moreover, a first band is observed in the visible which is much more intense for the compounds of the invention, as well as faster discoloration kinetics. It is also to be noted that the compound (1) of the invention has a UV band shifted further towards the visible which improves its sensitiveness to solar light.

What is claimed is:

1. Compounds of formula (I):

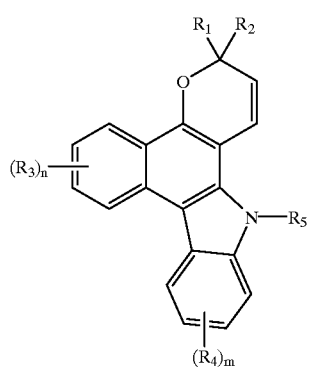

in which:

$R_1$ and $R_2$, identical or different, independently represent:
  hydrogen,
  a linear or branched alkyl group having 1 to 12 carbon atoms,
  a cycloalkyl group having 3 to 12 carbon atoms,
  an aryl or heteroaryl group having 6 to 24 carbon atoms or 4 to 24 carbon atoms respectively in its basic structure and at least one heteroatom selected from sulfur, oxygen and nitrogen; said basic structure optionally being substituted with at least one substituent selected from:
    a halogen,
    a linear or branched alkyl group having 1 to 12 carbon atoms,
    a linear or branched alkoxy group having 1 to 12 carbon atoms,
    a linear or branched haloalkyl or haloalkoxy group corresponding respectively to the $(C_1-C_{12})$alkyl and $(C_1-C_{12})$alkoxy groups above substituted with at least one halogen atom,
    a linear or branched alkenyl group having 2 to 12 carbon atoms,
    an $NH_2$ group,
    an NHR group, R representing a linear or branched alkyl group having 1 to 6 carbon atoms,
    a

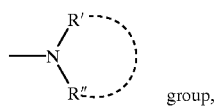

group,

R' and R", identical or different, representing independently a linear or branched alkyl group having 1 to 6 carbon atoms or representing, together with the nitrogen atom to which they are bound, a 5- to 7-membered ring which can comprise at least one other heteroatom selected from oxygen, sulfur and nitrogen, said nitrogen optionally being substituted with an R''' group, wherein the R''' group is a linear or branched alkyl group having 1 to 6 carbon atoms,
    an epoxy group of formula:

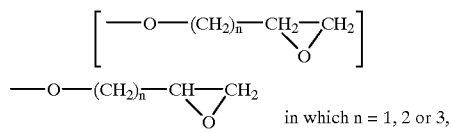

in which n = 1, 2 or 3, an aralkyl or heteroaralkyl group, the linear or branched alkyl group having 1 to 4 carbon atoms and the aryl and heteroaryl groups having the definitions given above, or
  said two substituents $R_1$ and $R_2$ together form an adamantyl, a norbornyl, a fluorenylidene, a di$(C_1-C_6)$alkylanthracenylidene or a spiro$(C_5-C_6)$cycloalkylanthracenylidene group; said group optionally being substituted with at least one of the substituents listed above for $R_1$, $R_2$: aryl or heteroaryl group;

$R_3$ represents:
  hydrogen,
  a linear or branched alkyl group having 1 to 12 carbon atoms,
  a cycloalkyl group having 3 to 12 carbon atoms,
  an linear or branched alkoxy group, having 1 to 12 carbon atoms,
  a haloalkyl, a halocycloalkyl or a haloalkoxy group corresponding respectively to the alkyl, cycloalkyl, or alkoxy groups above, substituted with at least one halogen atom,
  an aryl or heteroaryl group having the same definition as that given above for $R_1$, $R_2$,
  an aralkyl or heteroaralkyl group, the linear or branched alkyl group having 1 to 4 carbon atoms and the aryl and heteroaryl groups having the same definitions as those given above for $R_1$, $R_2$,
  an $-OCOR_6$ or $-COOR_6$ group, $R_6$ representing a straight or branched alkyl group having 1 to 6 carbon atoms or a cycloalkyl group having 3 to 6 carbon atoms or a phenyl group optionally substituted with at least one of the substituents listed above for the $R_1$, $R_2$ values: aryl or heteroaryl;

$R_4$ represents:
  hydrogen,
  a halogen,
  a linear or branched alkyl group having 1 to 12 carbon atoms,
  a cycloalkyl group having 3 to 12 carbon atoms,
  an linear or branched alkoxy group having 1 to 12 carbon atoms,
  a haloalkyl, a halocycloalkyl or a haloalkoxy group corresponding respectively to the alkyl, cycloalkyl, or alkoxy groups above, substituted with at least one halogen atom,
  an aryl or heteroaryl group having the same definition as that given above for $R_1$, $R_2$,
  an aralkyl or heteroaralkyl group, the linear or branched alkyl group having 1 to 4 carbon atoms and the aryl and heteroaryl groups having the same definitions as those given above for $R_1$, $R_2$, an amine or amide group: —NH$_2$, —NHR, —CONH$_2$, —CONHR,

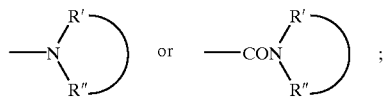

R, R', R" having their respective definitions given above for the amine substituents of the R$_1$, R$_2$ values: aryl or heteroaryl, an —OCOR$_6$ or —COOR$_6$ group, R$_6$ representing a straight or branched alkyl group having 1 to 6 carbon atoms or a cycloalkyl group having 3 to 6 carbon atoms or a phenyl group optionally substituted with at least one of the substituents listed above for the R$_1$, R$_2$ values: aryl or heteroaryl;

m and n are, independently, integers of 0 to 4;

R$_5$ represents:
hydrogen,
a linear or branched alkyl group having 1 to 12 carbon atoms,
a cycloalkyl group having 3 to 12 carbon atoms,
a linear or branched alkenyl group having 2 to 12 carbon atoms,
a phenyl or benzyl group, optionally substituted with at least one of the substituents listed above for the R$_1$, R$_2$ values: aryl or heteroaryl,
a —COR$_7$, —COOR$_7$ or —CONHR$_7$ group, R$_7$ representing a straight or branched alkyl group having 1 to 6 carbon atoms or a cycloalkyl group having 3 to 6 carbon atoms or a linear or branched alkenyl group having 2 to 12 carbon atoms or a phenyl or benzyl group optionally substituted with at least one of the substituents listed above for the R$_1$, R$_2$ values: aryl or heteroaryl,
a methacryloyl group or an acryloyl group,
an epoxy group of formula:

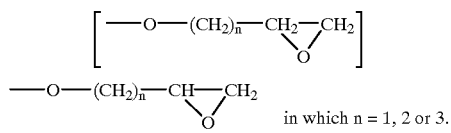

in which n = 1, 2 or 3.

2. The compounds according to claim 1, of formula (I1):

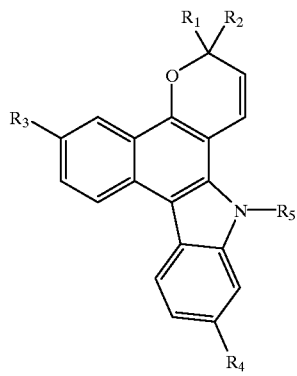

(I1)

in which:
R$_1$ and R$_2$, identical or different, independently represent optionally substituted aryl or heteroaryl groups whose basic structure is selected from those of the phenyl, naphthyl, biphenyl, pyridyl, furyl, benzofuryl, dibenzofuryl, N—(C$_1$–C$_6$)alkylcarbazole, thienyl, benzothienyl, dibenzothienyl and julolidinyl groups;

R$_3$ represents hydrogen, a linear or branched alkoxy group having 1 to 6 carbon atoms, a linear or branched alkyl group having 1 to 6 carbon atoms;

R$_4$ represents hydrogen, a linear or branched alkoxy group having 1 to 6 carbon atoms, a halogen, a linear or branched alkyl group having 1 to 6 carbon atoms, a morpholino group or a dialkylamino group —NR'R" in which R' and R" independently represent a linear or branched alkyl group having 1 to 6 carbon atoms; and R$_5$ represents hydrogen, a linear or branched alkyl group having 1 to 6 carbon atoms, an optionally substituted phenyl or benzyl group, a —COR$_7$, —COOR$_7$, or —CONHR$_7$ group, R$_7$ representing a straight or branched alkyl group having 1 to 6 carbon atoms or an optionally substituted phenyl or benzyl group.

3. A method of preparing compounds of formula (I) according to claim 1, characterised in that it comprises:
condensing a compound of formula (II):

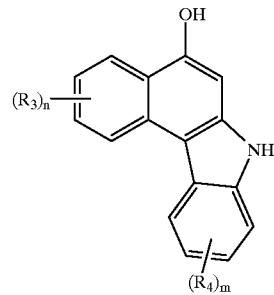

(II)

in which R$_3$, R$_4$, m and n are as defined in claim 1, with reference to formula (I); either
with a propargylic alcohol derivative of formula (III) below:

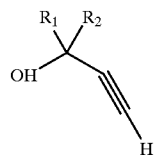

(III)

in which R$_1$ and R$_2$ are as defined in claim 1 with reference to formula (I); or
with, in the presence of titanium tetralkoxide, an aldehyde of formula (III') below

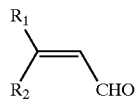

(III')

in which R$_1$ and R$_2$ are as defined in claim 1 with reference to formula (I); in order to obtain compounds of formula (I) in which R$_5$ represents hydrogen;

deprotonating, in the presence of sodium hydride, said compounds of formula (I) in which R$_5$ represents hydrogen and reacting them with an electrophilic compound of formula $R_5X$, in which $R_5$ is as defined in claim 1 but different from hydrogen and X is a leaving group, in order to obtain compounds of formula (I) in which $R_5$ is different from hydrogen.

4. A photochromic compound comprising a compound according to claim 1, or of a mixture of at least two compounds according to claim 1, or of a mixture of at least one compound according to claim 1 with at least one other photochromic compound of another type and/or at least one non-photochromic coloring agent.

5. A photochromic composition comprising:

at least one compound according to claim 1, and optionally, at least one other photochromic compound of another type and/or at least one non-photochromic coloring agent and/or at least one stabilizing agent.

6. An ophthalmic or solar article comprising:

at least one compound according to claim 1.

7. The article according to claim 6, wherein the article is constituted by a lens.

8. A glazing and/or optical device comprising:

at least one compound according to claim 1.

9. An ophthalmic or solar article comprising:

at least one composition according to claim 5.

10. The article according to claim 9, wherein the article is constituted by a lens.

11. A glazing and/or optical device comprising:

at least one composition according to claim 5.

* * * * *